United States Patent [19]
Grieshaber et al.

[11] Patent Number: 5,676,650
[45] Date of Patent: Oct. 14, 1997

US005676650A

[54] OPHTHALMOLOGIC ASPIRATION AND IRRIGATION SYSTEM, AND METHOD OF OPERATING SAME

[75] Inventors: Hans R. Grieshaber; Urs Vogel, both of Schaffhausen, Switzerland

[73] Assignee: Grieshaber & Co. AG Schaffhausen, Schaffhausen, Switzerland

[21] Appl. No.: 574,960

[22] Filed: Dec. 19, 1995

[30] Foreign Application Priority Data

Dec. 20, 1994 [CH] Switzerland ............... 03 832/94

[51] Int. Cl.$^6$ .......................... A61M 37/00; A61M 1/00
[52] U.S. Cl. .................. 604/28; 604/31; 604/119; 604/35; 417/205; 417/251
[58] Field of Search ................ 604/19, 27, 28, 604/30–31, 118–119, 35; 417/205, 251, 248, 313

[56] References Cited

U.S. PATENT DOCUMENTS

| | | | |
|---|---|---|---|
| 3,642,382 | 2/1972 | Huse | 417/205 |
| 4,274,411 | 6/1981 | Dotson, Jr. | 604/30 |
| 4,325,676 | 4/1982 | Fenne et al. | 417/251 |
| 5,039,280 | 8/1991 | Saulgeot et al. | 417/205 |
| 5,382,229 | 1/1995 | Grabenkort et al. | 604/27 |

*Primary Examiner*—Mark Bockelman
*Assistant Examiner*—Ellen Tao
*Attorney, Agent, or Firm*—Henry M. Feiereisen

[57] ABSTRACT

An aspiration and irrigation system of an ophthalmologic device for performing surgical operations on an eye of a living being, includes an irrigation unit for conducting a fluid under pressure to the eye via a first passageway, and an aspiration unit for simultaneous removal of fluid and/or tissue from the eye via a second passageway. The aspiration unit includes a two-stage pump system with a primary vacuum pump producing suction to effect a withdrawal of fluid and/or tissue from the eye through the second passageway and a secondary vacuum pump positioned downstream of the primary pump in a third passageway in communication with the second passageway, for boosting the suction pressure produced by the primary pump.

18 Claims, 3 Drawing Sheets

OPHTHALMOLOGIC ASPIRATION AND IRRIGATION SYSTEM, AND METHOD OF OPERATING SAME

BACKGROUND OF THE INVENTION

The present invention refers to an ophthalmologic aspiration and irrigation system for use in an ophthalmologic device for performing surgical operations on the eye of a living being. Moreover, the present invention refers to a method of operating an ophthalmologic aspiration and irrigation system.

European Pat. No. EP-A 0 596 314 discloses an ophthalmologic aspiration and irrigation system for performing surgical operations on an eye of a living being, by which the intraocular pressure can be adjusted and, if necessary e.g. in circumstances such as hemorrhaging or the like, momentarily increased with gaseous or liquid fluids. The aspiration and irrigation system includes an aspiration unit with a vacuum pump by which tissue and/or fluid is removed from the eye. A drawback of this system is the possible buildup during surgical procedure of an air cushion within the suction conduit that tends to delay the operation of the vacuum pump and thus adversely affects the effectiveness thereof.

SUMMARY OF THE INVENTION

It is an object of the present invention to provide an improved aspiration and irrigation system obviating the afore-stated drawbacks.

In particular, it is an object of the present invention to provide an improved aspiration and irrigation unit which enables rapid generation of a sufficiently high vacuum while still maintaining a required sterility.

It is a further object of the present invention to provide a method of operating an aspiration and irrigation unit.

These objects and others which will become apparent hereinafter are attained in accordance with the present invention by providing the aspiration system with a two-stage pump unit that is formed with a primary vacuum pump which produces a vacuum to effect a withdrawal of fluid and/or tissue from the eye and with a secondary vacuum pump which is positioned downstream of the primary vacuum pump for boosting the suction produced by the primary vacuum pump.

Through provision of a secondary booster pump to supplement the primary vacuum pump, the surgical procedure can be executed at a proper vacuum build up, and any air trapped in the primary pump system is safely removed to maintain a desired operation of the aspiration unit.

In accordance with the present invention, a method of operating an aspiration and irrigation system for use with an ophthalmologic device for performing surgical operations on an eye of a living being, includes the steps of removing tissue and/or fluid by suction via a first passageway and injecting fluid via a second passageway to replace withdrawn tissue, with the suction in the first passageway being generated by a two-stage pump unit with a primary pump system and a secondary pump system positioned downstream of the primary pump system; and regulating the suction by suitably controlling the secondary pump system such that an air cushion prevailing in the first passageway of the primary pump system is at least partially sucked off and removed.

BRIEF DESCRIPTION OF THE DRAWING

The above and other objects, features and advantages of the present invention will now be described in more detail with reference to the accompanying drawing in which.

DETAILED DESCRIPTION OF PREFERRED EMBODIMENTS

Figure 1:
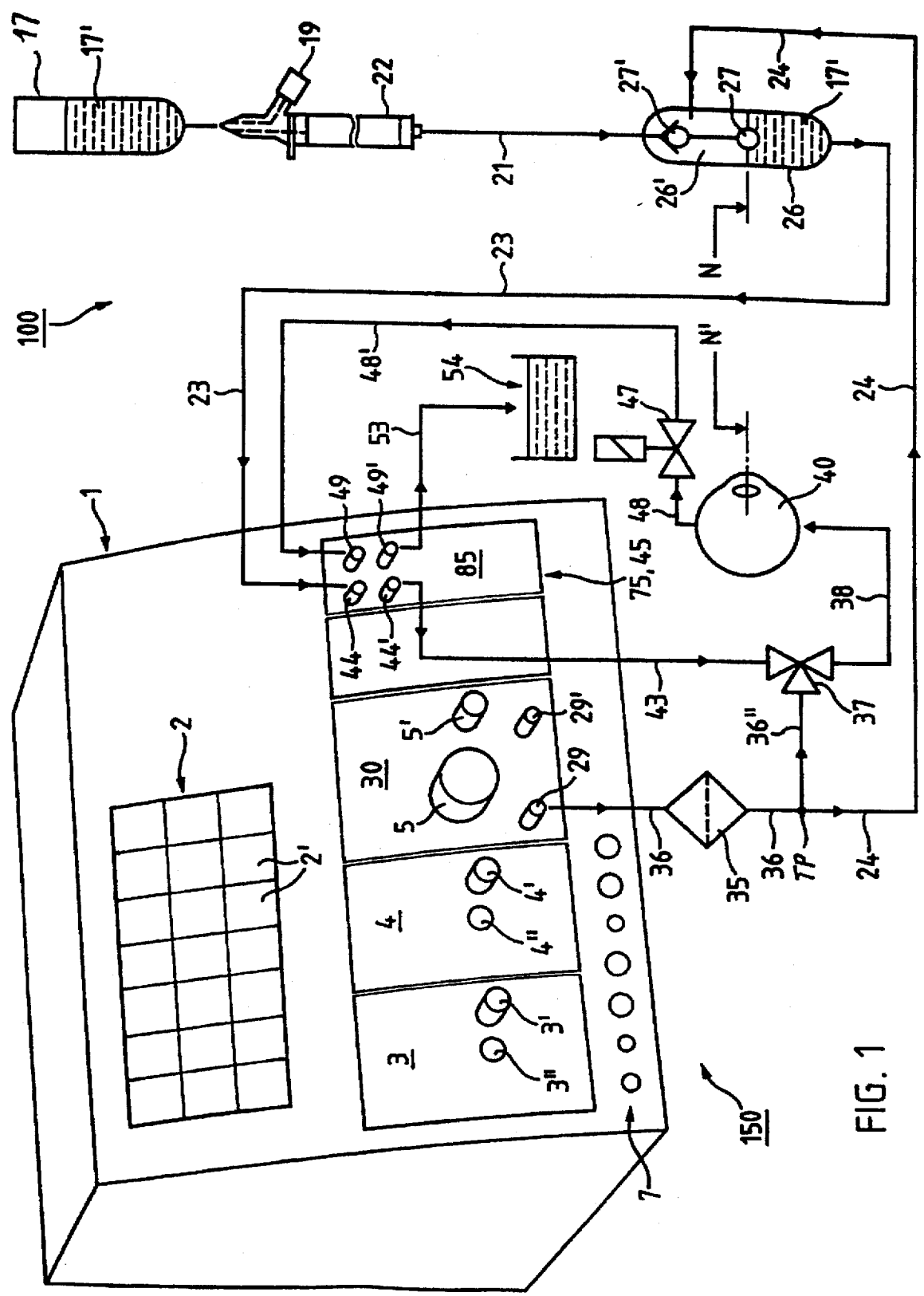
FIG. 1 is a simplified flow diagram to explain the control principle of an aspiration and irrigation system which is part of an ophthalmologic device illustrated in perspective view.

Referring now to the drawing, and in particular to FIG. 1, there is shown a schematic illustration of an aspiration and irrigation system according to the present invention which is part of an ophthalmologic device illustrated in perspective view and generally designated by reference numeral 150. The ophthalmologic device 150 is used for microsurgical operations on an eye 40 of a living being and includes a housing 1 with a front console comprised of several side-by-side compartments for receiving exchangeable functional units 3, 4, 30, 45, 75 which are designed in the form of plug-in cassettes 85 to serve particular surgical procedures. Below the compartments, the front face of the housing 1 is further provided with a multipoint connector 7 for enabling attachment of additional surgical instruments.

Both functional units 3, 4 constitute lighting units which illuminate the surgical site of the eye. The structure of such lighting units 3, 4 is generally known and may include an optical conductor with a light source on one end and an adapter on the other end for attachment to complementary jacks 3" and/or 4" on the front console of housing 1. During a surgical procedure, the light intensity of the lighting units 3, 4 can be continuously controlled by adjustment knobs 3' and 4'. The optical conductor together with the light source and adapter as well as much other additional apparatus such as electric circuits do not form part of the present invention and thus have been omitted from the drawing for sake of simplicity.

Arranged above the compartments, the console of the housing 1 is further provided with a display panel 2 which e.g. is subdivided into separate LCD fields 2' for indicating and controlling certain operations. The display panel 2 is part of a not shown computerized control system to provide the user with certain information of the ophthalmologic device 150, as well as to enable the user to manipulate procedures by touching respective fields 2' of the panel 2 and thus to initiate the selected program which is then illuminated.

As further indicated in FIG. 1, the functional units 30, 75, 45 are operatively connected with an aspiration and irrigation instrument which is generally designated by reference numeral 100 and described in more detail with reference to FIG. 2. The aspiration and irrigation instrument 100 is illustrated in FIG. 1 by way of a simplified flow diagram to explain the general control principle in order to ensure a simultaneous removal of fluid and/or tissue from the eye and replacement with fluid or gas.

The functional unit 30 which is situated next to the lighting unit 4 is a pressure gas supply unit for feeding a pressure gas such as compressed air to the surgical site and forms part of the aspiration and irrigation instrument 100. The functional unit or pressure unit 30 includes a connector 29 for attachment of a conduit 36 and an adjustment knob 5 for controlling, preferably continuously, the supply of compressed air to the surgical site for maintaining the required intraocular pressure of the eye. Preferably integrated within the housing 1 and operatively connected to the pressure unit 30 is a visco-injection device (not shown) which includes a connector 29' for attachment of a tube (not shown) and an adjustment knob 5' for control purposes.

Figure 2:
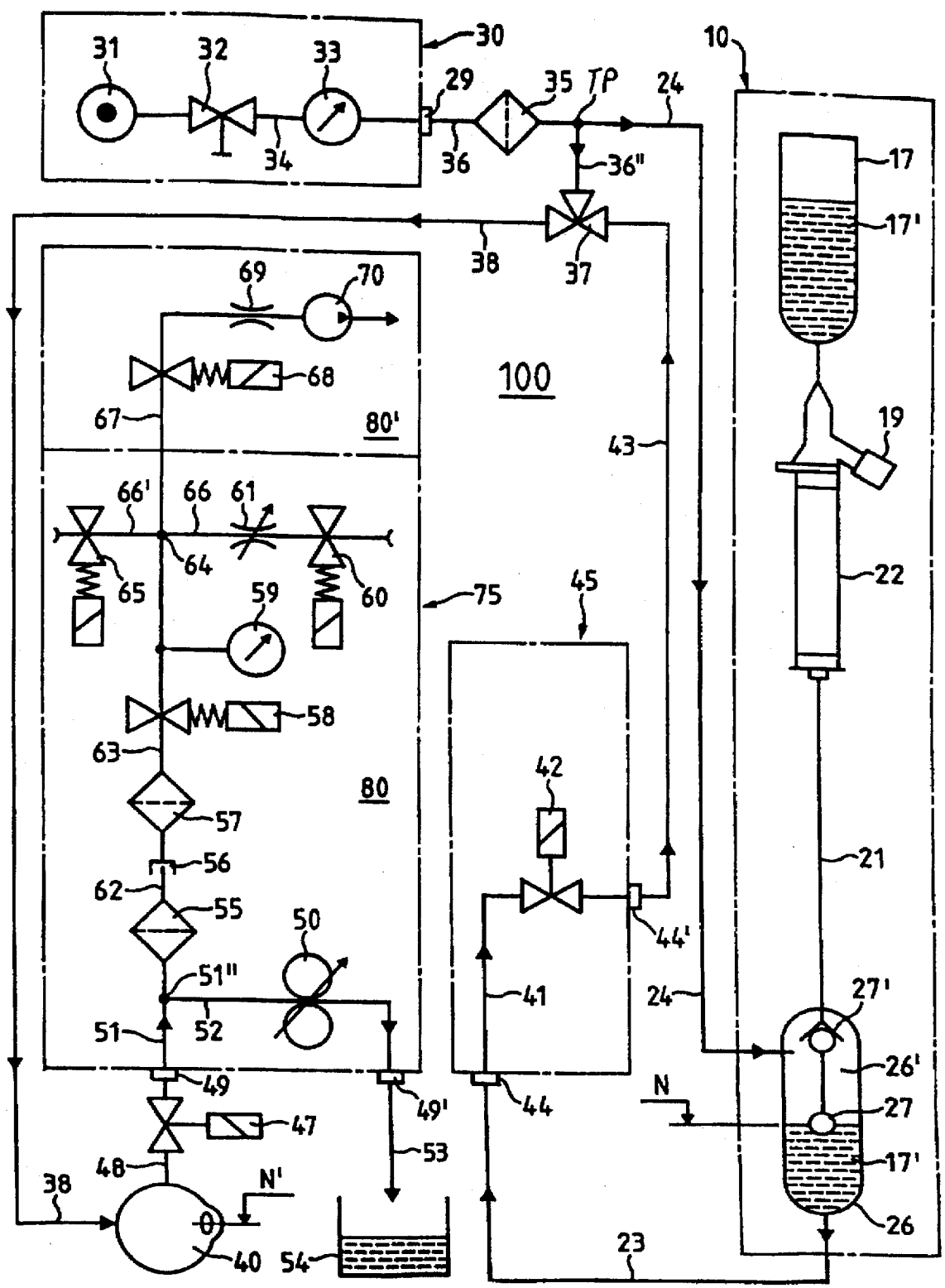
FIG. 2 is a complete flow diagram of the aspiration and irrigation system of FIG. 1.

The compartment next to the pressure unit receives a cassette system which contains the functional units 45 and 75, representing the irrigation unit 45 and the aspiration unit 75 and includes spaced connectors 44, 44' and 49, 49' for attachment of further functional units such as an infusion unit, generally designated by reference numeral 10 in FIG. 2 and essentially including a pair of successively arranged first and second infusion bottles 17, 26 with interposed dropper 22. The infusion bottle 17 contains a saline solution 17' and is connected via the dropper 22 with the infusion bottle 26 by a conduit 21. The dropper 22 may be of any suitable design and has a lateral branch for attachment of a filter 19 by which air drawn into the dropper 22 is sterilized. Saline solution 17' contained in the infusion bottle 26 exits the infusion bottle 26 through conduit 23 that is attached to the connector 44 of the irrigation unit 45. The level N of the saline solution 17' in the infusion bottle 26 is monitored by a float valve 27 which interacts with a control valve 27' so as to keep the level N constant and maintain it in alignment with the position-dependent level N' of the eye 40. It is of importance that during a surgical operation, both levels N and N' are at least approximately in alignment with each other, as indicated in FIG. 1.

During a drop of the fluid level N in the infusion bottle 26, an underpressure is generated in the dropper 22. When the fluid level N' falls below a predetermined minimum level, the float valve 27 opens the valve 27', effecting a flow of saline solution 17' from the infusion bottle 17 via the dropper 22 into the infusion bottle 26 while air sterilized by filter 19 is drawn into the infusion bottle 17 at the same time. As soon as the saline solution 17' in the infusion bottle 26 reaches the predetermined fluid level N, valve 27' closes again.

It will be appreciated by persons skilled in the art that the replenishing of liquid fluid 17' in the infusion bottle 26 as well as the opening and closing of the valve 27' is carried out automatically and attained under absolutely sterilized conditions.

As further shown in FIG. 1, the infusion bottle 26 communicates with the pressure unit 30 via a conduit 24 which enters with one end the space 26' of the infusion bottle 26 above the liquid level N and is connected with its other end to a connection point in the form of a T-piece TP for communication with the conduit 36 which is attached to the connector 29 of the pressure unit 30 via a filter 35 for sterilization of the pressure gas. Thus, sterilized compressed air is admitted into the space 26' of the infusion bottle 26 to pressurize the saline solution 17' contained therein.

Attached to the connector 44' of the irrigation unit 45 is one end of a conduit 43 which is connected with its other end to a multiport valve (three-way valve) 37 from which a conduit 38 leads to the eye 40. The connection point TP which unites the conduit 36 with conduit 24 is also linked to the multiport valve 37 by conduit 36". Thus, by suitably controlling the multiport valve 37, the eye 40 can be irrigated with sterilized compressed air from the pressure unit 30 via conduits 36", 38 or with sterilized liquid fluid such as saline solution 17' from the infusion bottle 26 via conduits 43, 38. Since pressure gas is also admitted to the infusion bottle 26 at a pressure set by the pressure unit 30, saline solution 17' can be supplied at a predetermined and continuously controllable pressure for maintaining the intraocular pressure (IOP).

Persons skilled in the art will understand that the conduit 24 may also be directly connected to the pressure unit 30 via a not shown connector so that sterilized compressed air can be directly admitted to the infusion bottle 26.

Turning now to FIG. 2, there is shown a complete flow diagram of the aspiration and irrigation system 100, with more detailed illustration of the relevant elements of the individual functional units 30, 45 and 75.

The pressure unit 30 includes a pressure gas source 31 and a control valve 32 for regulating the flow of pressure gas from the source 31 through a conduit 34. A pressure gage 33 measures the pressure in conduit 34 which is attached to the connector 29 of the pressure unit 30. The pressure as set by the control valve 32 is detected by the pressure gage 33 and the value commensurate with the pressure is displayed by one of the display fields 2'. If necessary, the pressure can be adjusted, e.g. continuously, by adjustment knob 5.

The irrigation unit 45 includes an interrupter element 42 which is positioned in a conduit 41 that links the connector 44 with the connector 44' and is suitably made e.g. of transparent, elastic material such as silicone or the like. The interrupter element 42 may be formed by a controllable solenoid valve with a not shown squeeze element by which the conduit 41 can be clamped to open or cut the fluid flow of liquid fluid 17' from the infusion bottle 26 to the eye 40.

Removal of fluid and tissue during a surgical operation from the eye is accomplished by the aspiration unit 75 which is provided in the form of a two-stage pump unit with a primary pump system 80 and a secondary pump system 80' which are connected to each other via a passageway formed by main conduits 63, 67.

The primary pump system 80 includes a vacuum pump 50, in the form of a booster pump such as a peristaltic pump, which is positioned in a conduit 52 that branches at connection point 51" off conduit 51 and is linked to the connector 49" so as to generate a suction in a conduit 48, thereby conducting tissue and fluid removed from the eye 40 through conduit 52 into a waste container 54 via a conduit 53. The vacuum pump 50 is suitably provided with (not shown) control elements for variably regulating the flow of air and fluid, and may be of the reciprocating type. An exemplified embodiment of a vacuum pump 50 is disclosed in European Pat. No. EP-A 0 601 313.

The primary pump system 80 is suitably connected to an instrument for pulverizing and removing a cataract via the conduit 48 which is attached to the connector 49 and made e.g. of transparent, elastic material such as silicone or the like. Preferably, an interrupter element 47 is interposed in the conduit 48 which may for example be a controllable solenoid valve with a not shown squeeze element by which the conduit 48 can be clamped to open or cut the flow of removed tissue through conduit 48. A typical instrument for pulverizing and removing a cataract is disclosed in European Patent No. EP-A 0 623 328.

Gaseous fluid withdrawn from the eye 40 by the vacuum pump 50 is conducted via conduit 48 and conduit 51 through a first filter 55 by which liquid fluid is separated, and sterilized conditions are maintained. The primary pump system 80 further includes downstream of the filter 55 a conduit 62 which is linked to a conduit 63 via a coupling 56. Interposed in the conduit 63 is a second filter 57 which is passed by gaseous fluid and ensures a complete separation of liquid fluid that may have escaped through the filter 55 so that functional components of the aspiration unit positioned downstream of the filter 57 are not subjected to any moisture. The flow of gaseous fluid through conduit 63 is controlled by a valve 58, with the pressure in the conduit 63 being measured by a pressure gage 59.

Preferably, the first filter 55, the connectors 49, 49'; 44, 44' and the conduits 51, 52, 62, 41 are part of a cartridge which is formed as tube carrier, as disclosed e.g. by European Pat. No. EP-A 0 601 313.

A ventilation of the primary pump system 80 is effected by a valve 60 which is positioned in a conduit 66 that branches off the conduit 63 at cross point 64. The valve 60 is preferably a throttle 61 to vent the primary pump system 80 in a throttled manner. The ventilation of the primary pump unit 80 can be accelerated (automatic reflux) by control of a further valve 65 which is positioned in a conduit 66' linked to the cross point 64. The valve 65 effects a complete ventilation of the aspiration system as soon as the vacuum collapses in the system. Such a vacuum collapse may occur when the ophthalmic surgical instrument becomes clogged by aggregating tissue particles or the like so that the suction pressure rises with running vacuum pump 50 to a maximum set value. When the clogging is dissolved, e.g. through sudden dissolution and withdrawal of the aggregating tissue particles, the vacuum may collapse. Such a vacuum collapse is suitably detected by electronic circuits (not shown) to effect simultaneously a complete ventilation through activation of the valve 65.

Positioned downstream of the primary pump system 80 is the secondary pump system 80' for adding additional suction pressure thereby discharging air that may still be trapped in the primary pump system 80. The secondary pump system 80' includes a vacuum pump 70 in the form of a booster pump which is connected to a conduit 67 that communicates with the conduit 63. The flow of gaseous fluid through conduit 67 is controlled by a valve 68 and a throttle 69. An activation of the booster pump 70 opens the valve 68, suitably in a time-delayed manner. A shutdown of the booster pump 70 automatically closes the valve 68.

As described above, the irrigation unit 45 and the aspiration unit 75 are parts of a plug-in cassette 85 that is pushed in the housing 1 to connect the conduit 52 of the aspiration unit 75 to the vacuum pump 50 and to connect the conduit 41 of the irrigation unit 45 to the solenoid valve 42.

The operation of the irrigation and aspiration instrument 100 is as follows:

During surgical procedure, the vacuum pump 50 applies a suitable suction pressure in the conduit 48 and conduits 51, 52 to draw fluid or tissue from the eye 40 into the waste container 54. An air cushion which builds up in conduit 48 and conduit 51 can be evacuated by the added suction pressure effected by the booster pump 50. Both pumps 50, 70 then run at a same time, with the booster pump 70 assuming the removal of air from the primary pump system 80.

According to a first mode of operation, the irrigation and aspiration instrument 100 operates at a desired pressure differential in the order of 100 to 600 mmHg (mercury column). Liquid fluid infused during surgical procedure to the surgical site of the eye 40 via conduit 38 is withdrawn together with tissue particles by the vacuum pump 50 at a desired value of the suction pressure while maintaining the required sensitiveness, and conducted to the waste container 54. The booster pump 70 is idle.

If added suction pressure is desired during the surgical procedure, e.g. from a minimum value to a maximum value, the booster pump 70 is activated in addition to the running vacuum pump 50. The activation of the booster pump 70 may be effected through actuation of a foot switch (not shown) that is operatively connected to the ophthalmologic device 150 when exceeding a desired pressure value difference. The booster pump 70 effects an evacuation of air from the primary pump system 80 so that the suction pressure is significantly increased in a relatively rapid manner.

After the primary pump system 80 is ventilated in a manner described above, the booster pump 70 remains idle until the surgeon re-adjusts the desired vacuum value to a minimum value. This prevents a premature activation of the booster pump 70 after an automatic ventilation is effected by the valve 65.

According to a second mode of operation, an actuation of the foot switch by the surgeon to operate the booster pump 70 in addition to the vacuum pump 50 is effected only in the event a predetermined desired vacuum value in the order of about 40 to 200 mmHg (mercury column) is exceeded. An automatic ventilation is thus omitted in this mode of operation.

Figure 3:
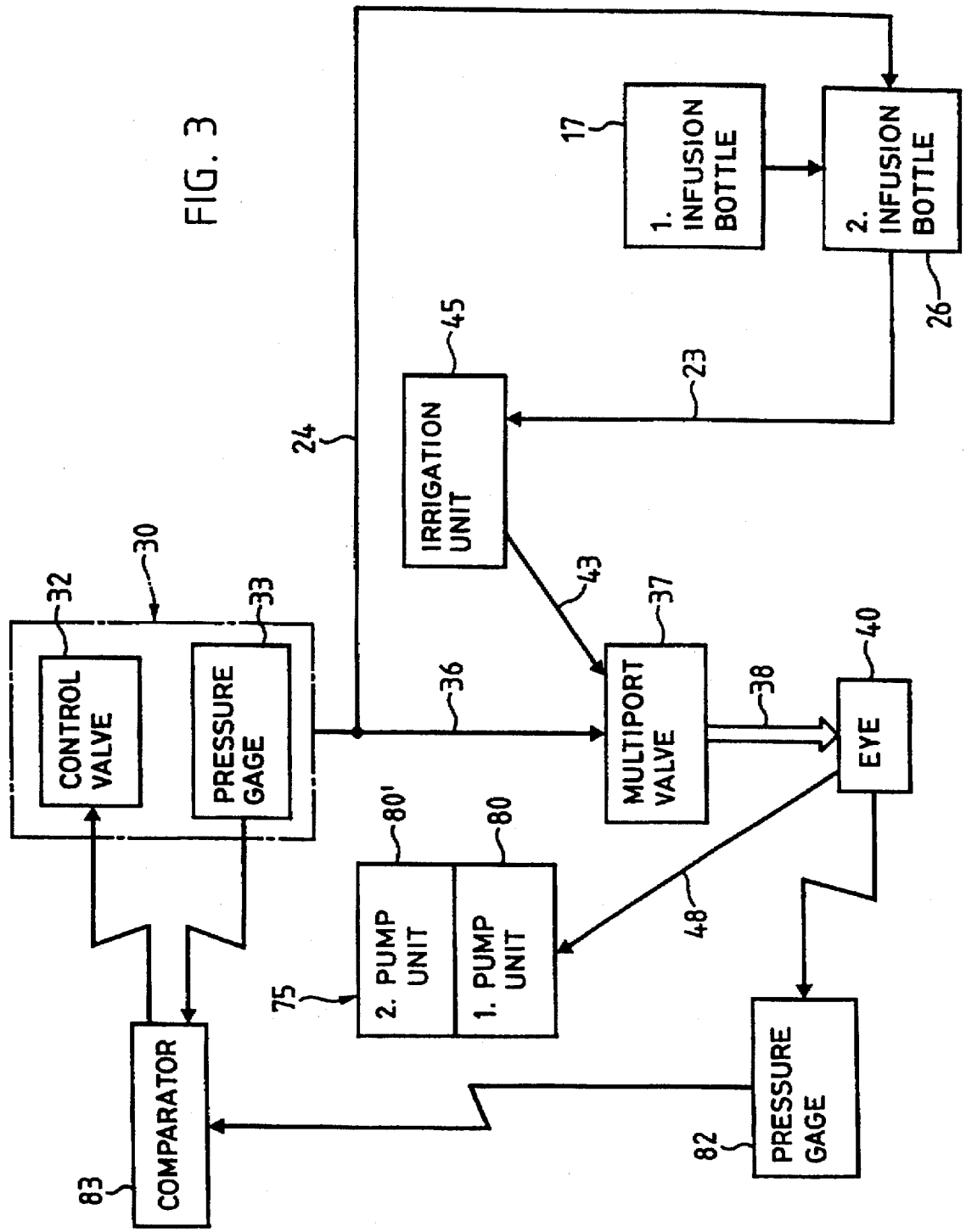
FIG. 3 is a simplified block diagram illustrating a general overview of the aspiration and irrigation system of FIG. 1.

Turning now to FIG. 3, there is shown a simplified block diagram illustrating a principal overview of the aspiration and irrigation system 100 of FIG. 1. Conduits 36, 38 define a first supply line through which sterilized gaseous fluid from the pressure unit 30 is conducted to the eye 40. Conduits 23, 43 form a second supply line for conducting liquid fluid to the eye 40. Conduit 24 which communicates with conduit 36 forms a third supply line by which sterilized, gaseous fluid is admitted into the infusion bottle 26 to pressurize liquid fluid 17' contained therein so that the flow of liquid fluid 17' to the eye 40 can be precisely controlled.

As further shown in FIG. 3 by way of example, a preferred embodiment of the present invention includes a pressure gage 82 by which the momentary intraocular pressure of the eye 40 is continuously monitored and suitably indicated on the display panel 2 of the ophthalmologic device 150. The actually sensed pressure is indicated on the display panel 2 and fed to a comparator 83 for comparison with a selected pressure. Thus, the pressure of the supplied gaseous or liquid fluid can be adjusted i.e. increased or decreased by setting the desired pressure on the display panel 2 (through slight finger pressure) for suitably adjusting the control valve 32 of the pressure unit 30.

Suitably, all conduits for gaseous and liquid fluids are made in the form of flexible tubes, preferably of transparent plastic material or the like. Both infusion bottles 17 and 26 of the infusion unit 10 as well as the dropper 22 should also be made of transparent plastic material.

In the non-limiting embodiment of the present invention, the individual functional units 3, 4, 30, 45 and 75 are provided in form of a cassette which are slidable into the respective compartments of the housing 1 of the ophthalmologic device 150. Persons skilled in the art will understand, however, that these individual functional units may however also be fitted in separate housings and respectively positioned.

While the invention has been illustrated and described as embodied in an ophthalmologic aspiration and irrigation system, and method of operating same, it is not intended to be limited to the details shown since various modifications and structural changes may be made without departing in any way from the spirit of the present invention.

What is claimed as new and desired to be protected by Letters Patent is set forth in the appended claims:

We claim:

1. An aspiration and irrigation system for use in an ophthalmologic device for performing surgical operations on an eye of a living being, comprising:

irrigation means for conducting a fluid under pressure to the eye via a first passageway;

aspiration means for simultaneous removal of fluid and/or tissue from the eye via a second passageway, said aspiration means comprising a two-stage pump system with a primary pump system including a primary vacuum pump producing suction to effect a withdrawal of fluid and/or tissue from the eye through the second passageway and a secondary pump system including a secondary vacuum pump positioned downstream of the primary pump system in a third passageway in communication with the second passageway for boosting the suction pressure produced by the primary vacuum pump, wherein the primary pump system includes a filter means for preventing a passage of liquid fluid, a valve arrangement and a pressure gage which are positioned downstream of the filter means to regulate a flow of gaseous fluid in response to a measurement by the pressure gage for ventilation of the aspiration means.

2. The aspiration and irrigation system of claim 2 wherein the primary pump system includes a first filter downstream of the valve for sterilizing withdrawn fluid, and a second filter arranged downstream of the first filter for separating remaining fluid.

3. The aspiration and irrigation system of claim 2 wherein the valve is provided with an interrupter element for cutting and opening a fluid flow through the second passageway.

4. The aspiration and irrigation system of claim 2 wherein the filter means of the primary pump system includes a first filter downstream of the valve for retention of liquid fluid, and a second filter arranged downstream of the first filter for separating remaining liquid fluid.

5. The aspiration and irrigation system of claim 5 wherein the valve arrangement includes a first throttle for effecting a throttled ventilation of the aspiration means.

6. The aspiration and irrigation system of claim 5 wherein the the secondary pump system includes a second throttle downstream of the first throttle to control suction effect generated by the secondary vacuum pump in addition to the suction generated by the primary vacuum pump.

7. The aspiration and irrigation system of claim 1 wherein the second pump system includes a valve in cooperation with a throttle to control a fluid flow through the third passageway.

8. The aspiration and irrigation system of claim 1 wherein the aspiration means with its functional elements downstream of the primary vacuum pump is formed as a structural unit which is operatively connectable to the primary vacuum pump.

9. The aspiration and irrigation system of claim 1 wherein the irrigation means includes a pressure unit for pressurizing the fluid conducted to the eye, said aspiration and irrigation system further comprising a pressure gage sensing a momentary intraocular pressure in the eye for providing a measuring signal commensurate with the momentary intraocular pressure, and a comparator receiving the measuring signal and comparing the measuring signal with a desired value for suitably controlling the pressure unit.

10. A method of operating an aspiration and irrigation system of an ophthalmologic device for performing surgical operations on an eye of a living being, comprising the steps of:

injecting fluid to a surgical site of the eye via a first passageway;

applying a surgical instrument for removing tissue and/or excess fluid by suction via a second passageway, with suction in the first passageway being generated by a two-stage pump unit comprised of a primary pump system and a secondary pump system which is positioned downstream of the primary pump system; and regulating the suction by suitably controlling the secondary pump system such that air prevailing in the first passageway of the primary pump system is at least partially sucked off and removed.

11. The method of claim 10 wherein the regulating step includes operating the secondary pump system in dependence on a predetermined desired pressure value.

12. The method of claim 11 wherein the operating step includes activating the secondary pump system when the predetermined desired pressure value is exceeded.

13. The method of claim 11 wherein the desired pressure value ranges from 100 to 600 mmHg (mercury column).

14. The method of claim 10 wherein the regulating step includes operating the secondary pump system at a predetermined desired pressure value for complementing the activated primary pump system.

15. The method of claim 14 wherein the desired pressure is in the order of 40 to 200 mmHg (mercury column).

16. The method of claim 10, and further comprising the steps of throttling and controlling the suction generated by the primary pump system.

17. The method of claim 10, and further comprising the step of closing and opening the first passageway by an interrupter element.

18. The method of claim 10, and further comprising the steps of sensing a momentary intraocular pressure in the eye for providing a measuring signal commensurate with the momentary intraocular pressure, and comparing the measuring signal with a desired value for adjusting a predetermined input signal.

\* \* \* \* \*

UNITED STATES PATENT AND TRADEMARK OFFICE
CERTIFICATE OF CORRECTION

PATENT NO. : 5,676,650
DATED : October 14, 1997
INVENTOR(S) : Hans R. Grieshaber & Urs Vogel It is certified that error appears in the above-identified patent and that said Letters Patent is hereby corrected as shown below:

Claim 5, column 7, line 34, change "5" to --1--; and

Signed and Sealed this

Twenty-first Day of April, 1998

Attest:

BRUCE LEHMAN

Attesting Officer

Commissioner of Patents and Trademarks